US010605733B1

United States Patent
Wu et al.

(10) Patent No.: US 10,605,733 B1
(45) Date of Patent: Mar. 31, 2020

(54) LIGHT SHEET IMAGING FLOW CYTOMETER

(71) Applicant: Verily Life Sciences LLC, Mountain View, CA (US)

(72) Inventors: Cheng-Hsun Wu, Mountain View, CA (US); Brian M. Rabkin, Redwood City, CA (US); Supriyo Sinha, Menlo Park, CA (US); John D. Perreault, Mountain View, CA (US); Chinmay Belthangady, San Francisco, CA (US); James Higbie, South San Francisco, CA (US); Seung Ah Lee, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 194 days.

(21) Appl. No.: 15/833,677

(22) Filed: Dec. 6, 2017

Related U.S. Application Data

(60) Provisional application No. 62/434,994, filed on Dec. 15, 2016.

(51) Int. Cl.
  *G06K 9/00* (2006.01)
  *G01N 21/64* (2006.01)
  *G01N 15/14* (2006.01)
  *A61B 1/00* (2006.01)

(52) U.S. Cl.
  CPC ..... *G01N 21/6458* (2013.01); *A61B 1/00188* (2013.01); *G01N 15/1434* (2013.01); *G01N 2015/1402* (2013.01); *G01N 2015/1445* (2013.01)

(58) Field of Classification Search
  CPC .......... G01N 21/6458; G01N 15/1434; G01N 2015/1402; G01N 2015/1445; A61B 1/00188
  See application file for complete search history.

(56) References Cited

U.S. PATENT DOCUMENTS

| | | | |
|---|---|---|---|
| 2004/0067167 A1 | 4/2004 | Zhang et al. | |
| 2014/0353522 A1 | 12/2014 | Wu et al. | |
| 2016/0146799 A1* | 5/2016 | Robinson | ......... G01N 33/54346 506/4 |
| 2016/0327779 A1* | 11/2016 | Hillman | ............... G02B 21/367 |

(Continued)

OTHER PUBLICATIONS

Wu, J. et al., "A Fast Fluorescence Imagining Flow Cytometer for Phytoplankton Anylysis", Optics Express, vol. 21, No. 20, Oct. 7, 2013, 6 pages.

(Continued)

*Primary Examiner* — Tom Y Lu
(74) *Attorney, Agent, or Firm* — Christensen O'Connor Johnson Kindess PLLC

(57) ABSTRACT

The present disclosure relates to systems and methods for cellular imaging and identification through the use of a light sheet flow cytometer. In one implementation, a light sheet flow cytometer may include a light source configured to emit light having one or more wavelengths, at least one optical element configured to form a light sheet from the emitted light, a microfluidic channel configured to hold a sample, and an imaging device. The imaging device may be adapted to forming 3-D images of the sample such that identification tags attached to the sample are visible.

19 Claims, 11 Drawing Sheets

(56) References Cited

U.S. PATENT DOCUMENTS

2017/0209864 A1* 7/2017 Grisham .......... B01L 3/502746
2019/0101537 A1* 4/2019 Weitz ................ B01L 3/502792

OTHER PUBLICATIONS

Rendall, H. et al., "High-throughput Optical Injection of Mammalian Cells Using a Bessel Light Beam", Lab on a Chip, Oct. 2012, 6 pages.
Regmi, R. et al., "MRT Letter: Light Sheet Based Imaging Flow Cytometry on a Microfluidic Platform", Microscopy Research and Technique vol. 76, 2013, 7 pages.
Wu, J. et al., "A Light Based High Throughput 3D-imaging Flow Cytometer for Phytoplankton Anylysis", Optics Express, vol. 21, No. 12, Jun. 17, 2013, 7 pages.

* cited by examiner

US 10,605,733 B1

LIGHT SHEET IMAGING FLOW CYTOMETER

CROSS-REFERENCE TO RELATED APPLICATIONS

This application claims the benefit of U.S. Provisional Application No. 62/434,994, filed Dec. 15, 2016, which is incorporated by reference in its entirety.

TECHNICAL FIELD

This disclosure relates generally to the field of imaging and microscopy systems and methods. More specifically, and without limitation, this disclosure relates to systems and methods for cellular imaging through the use of a flow cytometer incorporating a light sheet microscope and microfluidic channels.

BACKGROUND

Imaging flow cytometry couples a microscope with a microfluidic channel in order to image a sample, such as individual cells. The most advanced commercial imaging flow cytometer is presently the Amnis® system, which captures widefield images of the sample while the sample flows in a microfluidic channel. Widefield imaging, however, often has reduced contrast due to contamination from the out-of-focus background. Other microscopy techniques, like confocal and multiphoton, can produce images with higher contrast but are difficult to adapt to use in flow cytometry due to their slower frame rates and use of point scanning. The use of a light sheet microscope instead of widefield imaging results in an image with higher contrast but also permits the use of a higher frame rate than even a confocal microscope. The use of a light sheet microscope also permits for the construction of a three-dimensional (3-D) image of the individual cells with lower phototoxicity than a confocal microscope.

Light sheet microscopy functions by generating a thin (generally on the order of 1 μm) sheet of light that passes through the flowing fluid. This thin sheet captures a single plane of the sample as it passes through the sheet. Because the frame rate on the light sheet microscope is very high, rapid capture of successive planes of the sample is possible, permitting the construction of the three-dimensional image.

SUMMARY

At present, there is no available method to connect images of a sample with a prior sequencing of that sample. The use of a light sheet microscope in imaging flow cytometry may be coupled with various tagging techniques in order to solve this problem. Thus, if a sample is sequenced using a known method such as DropSeq, 10× genomics, 454 sequencing, or another known method using bead-bound oligonucleotides for capturing and analyzing genomic or transcriptional information (whether in a droplet or on a pico-titer plate), those cells may be tagged using fluorescent beads, barcodes, or other available tagging techniques and then imaged via light sheet microscopy. The images of the sample would then be connected to the sequences of that sample via the tags, which would be visible because the light sheet microscope can produce 3-D images with minimal photobleaching.

There are many possible applications for such capabilities. Examples of applications include observation of how different gene sequences result in different intracellular structures and interactions, such as phagocytosis, mitosis, signaling, autophagy, and morphology, and observation of cellular phenotypic manifestations of genotypic differences.

Certain embodiments of the present disclosure relate to systems and methods that improve the quality of microfluidic images by the use of a light sheet microscopy. The use of light sheet microscopy overcomes both image contrast and frame rate limitations in conventional imaging flow cytometers using widefield imaging, confocal microscopy, and multiphoton microscopy. The use of light sheet microscopy also produces a three-dimensional (3-D) image with minimal photobleaching.

According to an exemplary embodiment of the present disclosure, a light sheet flow cytometer is described. The system may include a light sheet microscope, an illumination objective, a detection objective, a microfluidic channel, and an imaging device.

According to a yet further exemplary embodiment of the present disclosure, a method for configuring a light sheet flow cytometer to obtain a 3-D image of a sample is described. The method includes the steps of providing a light source, forming a light sheet from the light source, illuminating a sample in a microfluidic channel, and imaging the emission light collected from successive planes to form a 3-D image of the sample.

Certain embodiments of the present disclosure relate to systems and methods that are adapted to coupling the sequencing of a sample with images of the sample. The use of light sheet microscopy permits three-dimensional (3-D) imaging of the sample such that the identification tag attached to the sample is visible. The visibility of the identification tag permits the images of the sample to be matched with a sequencing of the same sample.

According to a yet further exemplary embodiment of the present disclosure, a light sheet flow cytometer adapted to image a tagged sample is described. The system may include a tagging assay, a light sheet microscope, an illumination objective, a detection objective, a microfluidic channel, and an imaging device. The tagging assay may be included in a sequencing assay such that tagging and sequencing occur simultaneously.

According to a yet further exemplary embodiment of the present disclosure, a method for configuring a light sheet flow cytometer to obtain a 3-D image of a tagged sample is described. The method includes the steps of attaching an identification tag to the sample, providing a light source, forming a light sheet from the light source, illuminating the sample in a microfluidic channel, imaging the emission light collected from successive planes to form a 3-D image of the sample, and matching the images of the sample to other information related to the sample using the identification tags.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

One embodiment may include a system for an imaging flow cytometer, comprising a light source configured to emit light having one or more wavelengths, at least one optical element adapted to form a light sheet from the emitted light, an illumination objective, a microfluidic channel within the focus of the light sheet and configured to hold a sample, a detection objective, and an imaging device. The imaging device may be adapted to capture the light from the sample to image a two-dimensional plane of the sample. The imaging device may be further adapted to form a three-dimensional image from successive planar images. The imaging device may be further adapted to image identification tags contained within the sample.

An illustrative method of imaging a sample can include attaching identification tags to a sample, providing a light source that emits light having one or more wavelengths, forming a light sheet from the emitted light, directing the light sheet toward a microfluidic channel within the focus of the light sheet and configured to hold the sample containing identification tags, imaging emitted light collected from the sample, and rendering a three-dimensional image of the sample from successive two-dimensional images. Each two-dimensional image may portray a two-dimensional plane of the sample. The identification tags may be visible in the three-dimensional image.

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the disclosed principles. In the drawings.

DETAILED DESCRIPTION

Figure 1:
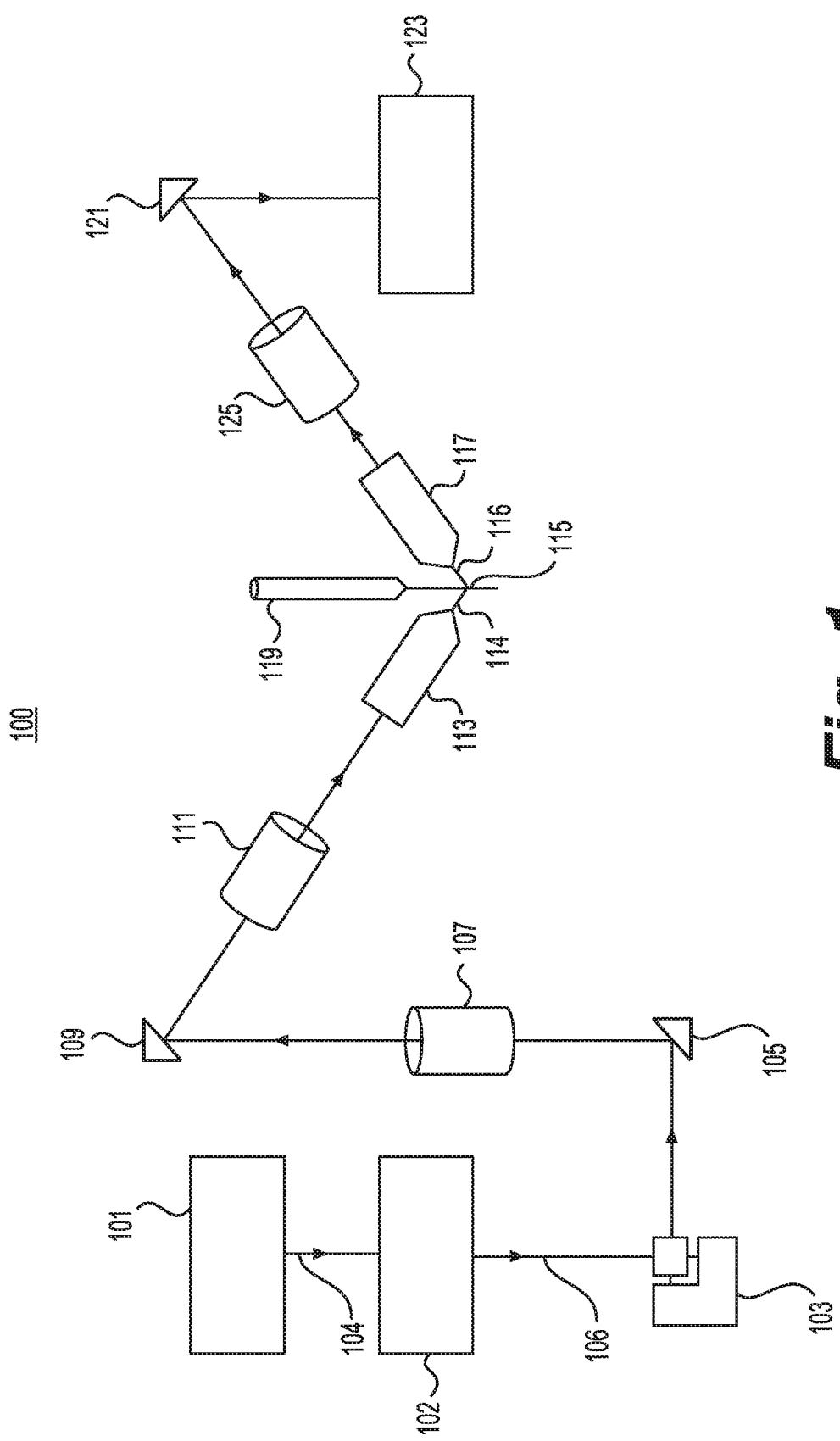
FIG. 1 is a schematic representation of an exemplary flow cytometer imaging system, according to embodiments of the present disclosure.

The disclosed embodiments relate to systems and methods for cellular imaging. Embodiments of the present disclosure may be implemented using a light sheet microscope. Alternatively, a flow cytometer imaging system may be built according to embodiments of the present disclosure using suitable optical elements.

Advantageously, embodiments of the present disclosure allow for acquiring a high-resolution 2-D image of a focal plan in a sample using a light sheet microscope. A plurality of 2-D images can be acquired at a plurality of focal planes and reconstructed to obtain a 3-D image of a sample. Additionally, embodiments of the present disclosure allow for attaching identification tags to a sample and reading identification tags in a sample.

According to an aspect of the present disclosure, excitation light having one or more wavelengths may be used as the basis for forming a light sheet. The excitation light may be emitted by a single-color source or a multi-color light source. In some embodiments, the single-color light source may be a pulsed or continuous laser that emits lights with a very narrow spectrum. In other embodiments, the single-color light source may be the output of a monochromator.

In some embodiments, the multi-color light source may have a continuous spectrum. For example, the multi-color lights source may be a broadband light source, such as certain supercontinuum lasers, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous lasers that emit light with very narrow spectra.

According to an aspect of the present disclosure, excitation light emitted by the light source may be directed to a set of optical elements adapted to form a light sheet. The light sheet may include a single sheet or a stack of sheets. The light sheet may be single- or multi-colored.

In some embodiments, the light sheet may be formed by dithering a Gaussian beam. For example, the set of optical elements for dithering a Gaussian beam may include any number of laser scanners, an f-theta lens, and a tube lens.

In other embodiments, the light sheet may include a lattice light sheet formed from a Bessel beam. For example, the set of optical elements for forming a lattice light sheet may include any number of cylindrical lenses, a beam splitter, a wave plate, a spatial light modulator, a mask, and any number of galvos.

In other embodiments, the light sheet may be formed by focusing a Gaussian beam. For example, the set of optical elements for focusing a Gaussian beam may include a collimator and a cylindrical lens.

In other embodiments, the light sheet may be formed by applying a Gaussian beam to a slit. For example, the set of optical elements may include a cylindrical beam expander, a rectangular slit, and any number of lenses.

According to an aspect of the present disclosure, a light sheet directed toward a sample may induce an emission pattern. In some embodiments, the emission pattern may be detected as forward-scattered light. In other embodiments, the emission pattern may be detected as side-scattered light.

As described herein, the excitation light may be focused by an illumination objective, and the emission light may be focused by a detection objective. The illumination and detection objectives may be separate, or they may be configured to operate in a dual-view illumination mode.

According to an aspect of the present disclosure, a sample may be contained within a microfluidic channel. In some embodiments, the channel may include microcapillaries. Advantageously, microcapillaries may allow the use of inlet microfluidic channels, which may be used for hydrodynamics focusing. In other embodiments, the channel may include microfluidic chips.

In some embodiments, the microfluidic channel may be sized on the order of the size of a sample. Advantageously, sizing the microfluidic channels on the order of the size of a sample may increase the friction between the sample and the channel, which may reduce rotation of the sample while passing through the light sheet.

In other embodiments, the microfluidic channel may include a low viscosity solution. Advantageously, a low viscosity solution may reduce shear force on a sample, which may reduce rotation of the sample while passing through the light sheet.

Other embodiments may include optical tweezers. Advantageously, optical tweezers may reduce rotation of the sample while passing through the light sheet.

According to an aspect of the present disclosure, emission light from the sample may be imaged by an imaging device to form a 2-D image. The imaging device may include an sCMOS camera or any suitable camera that allows for capture of a 2-D image from emission light.

In some embodiments, the light sheet may be multi-colored, and the imaging device may include a plurality of dichroic filters. The plurality of filters may be configured to direct different colors of emission light to different cameras. In other embodiments, the light sheet may be multi-colored, and the imaging device may include a filtering device. The filtering device may include a filter wheel or a liquid crystal filter and may be configured to select an emission spectral band to direct to a camera. In other embodiments, the light sheet may include a stack of light sheets, each sheet including different colors, and the imaging device may include multiple cameras, each corresponding to a different sheet.

Some embodiments may include a switch adapted to pulse the light sheet such that only selected planes of a sample are illuminated. The switch may include an acousto-optic deflector, optical shutter, or other suitable device that allows for a light sheet to be pulsed.

Some embodiments may include a second imaging device adapted to image the sample before it passes through the light sheet. For example, the second imaging device may include a widefield camera or any other device suitable for imaging a sample. Advantageously, the second imaging device may allow effective selection of illumination planes using a switch. Additionally, the second imaging device may allow correction of the images from the first imaging device caused by rotation of a sample.

According to an aspect of the present disclosure, a sample in a microfluidic channel may be flowed through a light sheet. In some embodiments, this flow may be induced using a pressure pump, syringe pump, peristaltic pump, electro-osmotic pump, pierzoelectric pump, or any other suitable pump. In other embodiments, this flow may be induced using a DC electric field. Advantageously, the use of a DC electric field may reduce rotation of the sample while passing through the light sheet.

According to an aspect of the present disclosure, systems and methods allow for 3-D imaging from 2-D images formed by successive light sheets. In some embodiments, the imaging device may be operably connected to a controller having a processor and a computer-readable medium that stores instructions or operational steps. These instructions or steps, when executed by the processor, may produce a 3-D image from the 2-D images captured by the imaging device. For example, the processor may use intrinsic and/or extrinsic properties of the captured emission light as recorded by the imaging device to determine the depths of the successive 2-D images, may construct a depth mesh corresponding to the determined depths, and may project the successive 2-D images onto the constructed depth mesh. In certain aspects, the instructions or steps, when executed by the processor, may further post-process the 2-D images prior to production of the 3-D image and may further post-process the produced 3-D image. Post-processing may include, for example, reduction of optical aberrations; adjustment of brightness, contrast, etc.; or smoothing the textures.

In some embodiments, the 2-D images may be constructed over time as a sample flows through a microfluidic channel. For example, the processor may store the 2-D images collected over time and may render a single 3-D image from successively stored 2-D images.

In other embodiments, the light source and set of optical elements may produce a stack of light sheets, which may be used to produce simultaneous 2-D images that may be post-processed to produce a 3-D image. In certain aspects, the imaging device may include a light field camera. Advantageously, light field cameras record information about the direction of the captured light in additional to the intensity of the captured, which may facilitate formation of a 3-D image from successive 2-D images. In other aspects, the imaging device may be adapted to execute swept, confocally-aligned planar excitation (SCAPE) microscopy. Preferably, the imaging device may include at least one mirror adapted to generate an oblique image plane from the emission light and may include a high-speed 2-D camera, which may capture the oblique image plane.

In other aspects, the imaging device may be adapted to execute axial plane optical microscopy (APOM). Preferably, the imaging device may include at least one mirror and at least one lens, adapted to capturing both the lateral plane and the axial plane from the emission light, and may include a CCD camera.

In other embodiments, the detection objective may be coupled to a translation stage, which may be adapted to move the detection objective through the stack of light sheets. The stage may be a motorized translation stage, a nanopositioning piezo stage, or any suitable stage that allows for lateral linear movement. In certain aspects, the processor may be operably connected to the stage in addition to the imaging device. The instructions or steps, when executed by the processor, may synchronize the movement of the stage with the capture of 2-D images from the imaging device. The processor may store the 2-D images collected with the movement of the stage and may render a single 3-D image from successively stored 2-D images.

Some embodiments may include a Shack-Hartmann wavefront sensor. The sensor may measure the aberrations from the microfluidic channel. Some embodiments may include custom phase plates to correct the measured aberrations. Other embodiments may include post-processing of the images from the imaging device using the Gerchberg-Saxton algorithm to correct the measured aberrations.

Other embodiments may include spatial light modulators to measure the point spread function from the microfluidic channel and adaptively correct aberrations.

In other embodiments, the microfluidic channel may be adapted to minimize aberrations. For example, the channel may be constructed to avoid spherical or curved focusing surfaces or may include a material with a refractive index which matches that of the fluid within the channel.

Other embodiments may include water or oil immersion objectives. The immersion objectives may reduce aberrations from the channel.

According to an aspect of the present disclosure, an identification tag attached to the sample may be visible in the 3-D image. Advantageously, forming a 3-D image from successive, high-resolution 2-D images may permit rendering of a high-resolution 3-D image, which may increase the visibility of the identification tag within the 3-D image.

In some embodiments, the identification tag may include a plurality of beads. The beads may be fluorescent beads or any other beads adapted to being read on the 3-D image. The plurality of beads may be spatially arranged in a well-defined fashion and may be strung together by a backbone. For example, one identification tag may include a red bead followed by a blue bead followed by a green bead, and a different identification tag may include a red bead followed by a yellow bead followed by a purple bead. The possible number of codes may increase exponentially as the number of beads in the plurality of beads increases. Advantageously, pattern ambiguity in the imaged sample may be reduced, as compared with traditional flow cytometry images, by using high-resolution 3-D images to render the identification tag visible.

In other embodiments, the identification tag may include at least one bead. The beads may be photobleachable beads or any other beads adapted to having a barcode printed thereon. For example, spatial selective photobleaching may have the ability to encode up to $10^8$ different barcodes on a 50 μm bead. The possible number of codes may be increased by increasing the number of beads containing barcodes. Advantageously, pattern ambiguity in the imaged sample may be reduced, as compared with traditional flow cytometry images, by using high-resolution 3-D images.

In some embodiments, the identification tag may be associated with a prior sequencing of the sample. In certain aspects, the identification tag may be attached when the sample is sequenced. For example, the sample may be sequenced using DropSeq, which attaches the copied sequence from the sample onto a bead or series of beads. By way of further example, the sample may be sequenced using 10× genomics, 454 sequencing, or another known method using bead-bound oligonucleotides for capturing and analyzing genomic or transcriptional information (whether in a droplet or on a pico-titer plate). The bead or series of beads used in these technologies may function as the identification tag, for example, by containing a barcode thereon. Advantageously, the sequence of the sample may then be identified by the bead or series of beads that was used, and the 3-D image of the sample may also be identified by the same bead or series of beads that is visible in the image.

In some embodiments, the association may be performed by a controller having a processor and a computer-readable medium that stores instructions or operational steps. These instructions or steps, when executed by the processor, may perform the association. For example, the processor may identify the location in the 3-D image where the identification tag is visible, may extract the data from the identified location, and may identify the stored sequence whose identification tag matches the extracted data.

Reference will now be made in detail to exemplary embodiments and aspects of the present disclosure, examples of which are illustrated in the accompanying drawings.

FIG. 1 is a schematic representation of an exemplary flow cytometer imaging system 100. As shown in FIG. 1, system 100 may include a light source 101, a set of optical elements 102, an illumination objective 113, a microfluidic channel 119, a detection objective 117, and an imaging device 123. Microfluidic channel 119 may contain a sample 115. System 100 may further include a scanner 103, one or more mirrors, e.g., mirrors 105, 109, and 121, and one or more lenses, e.g., lenses 107, 111, and 125. System 100 may include other optical elements, such as mirrors, beam dumps, spatial filters, an x-y translation stage, a z-axis translation stage, a tunable liquid lens (not shown), etc.

In flow cytometer imaging system 100, as shown in FIG. 1, light source 101 may emit excitation light 104. A set of optical elements 102 may form a light sheet 106 from excitation light 104. In some embodiments, light sheet 106 may pass through a scanner 103, may pass through one or more mirrors, e.g., mirrors 105, 109, and 121, or may pass through one or more lenses, e.g., lenses 107, 111, and 119, before reaching illumination objective 113. Objective 113 may focus the light sheet 106 to an illumination light sheet 114 directed at a sample 115 that may be contained within a microfluidic channel 119.

Figure 2:
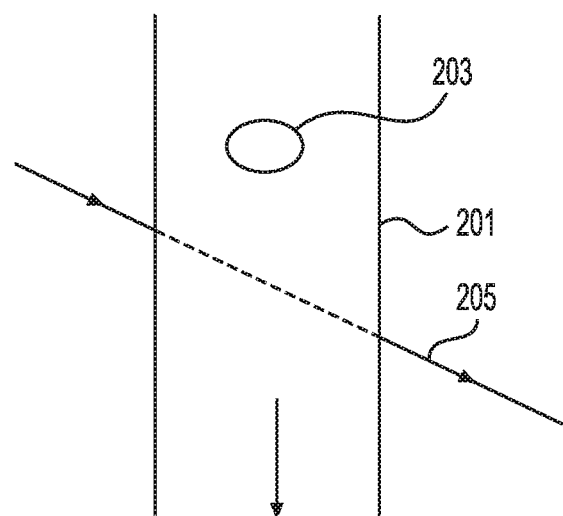
FIG. 2 is a schematic cross-sectional illustration of an example of a light sheet passing through the sample of the exemplary flow cytometer of FIG. 1, according to embodiments of the present disclosure.

FIG. 2 is a schematic cross-sectional illustration of an exemplary embodiment of illumination light sheet 114 passing through sample 115 of exemplary flow cytometer 100 of FIG. 1. As shown in FIG. 2, light sheet 205 may pass through a single plane of microfluidic channel 201. Sample 203 may flow in the direction shown in FIG. 2 and thereby pass through the light sheet.

In exemplary flow cytometer imaging system 100, as shown in FIG. 1, illumination light sheet 114 may induce emission light 116 from sample 115. Emission light 116 may be collected and/or focused by detection objective 117. In some embodiments, emission light 116 may pass through one or more lenses, e.g., lens 125, and one or more mirrors, e.g., mirror 121, before reaching imaging device 123.

Functions and the working principles of various components of the system are described in detail below.

As described above, light source 101 may be a single-color light source or multi-color light source. Additionally or alternatively, light source 101 may include multiple light sources, of which each may be single- or multi-color.

In some embodiments, light source 101 may be operably connected to a controller (not shown) having a processor and a computer-readable medium that stores instructions or operational steps. These instructions or steps, when executed by the processor, may modulate the operational states of light source 101. For example, the processor may activate or deactivate light source 101, modulate the duration of a pulse of a pulsed light source 101, and/or switch or tune the emission wavelengths of light source 101.

In some embodiments, imaging device 123 may be operably connected to a controller (not shown) having a processor and a computer-readable medium that stores instructions or operational steps. These instructions or steps, when executed by the processor, may produce a 3-D image from the 2-D images produced by imaging device 123. For example, the processor may store the 2-D images collected over time, may render a single 3-D image from successively stored 2-D images, and may increase the clarity of the 3-D image, for example, by correcting for optical differences between successive 2-D images.

Figure 3:
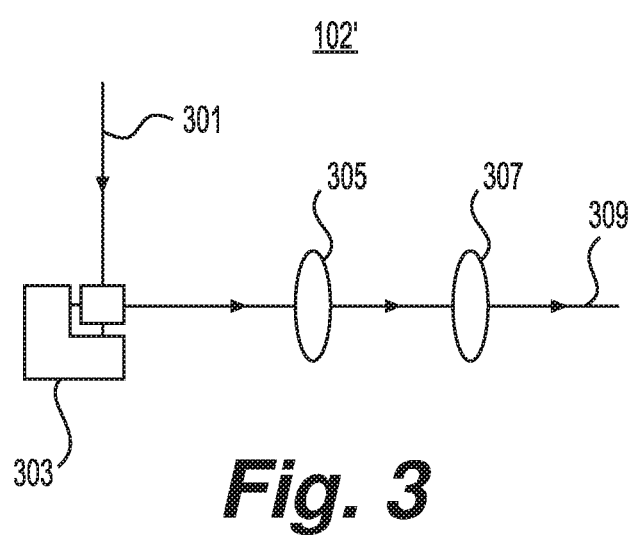
FIG. 3 is a schematic representation of an exemplary set of optical elements for forming the light sheet for the exemplary flow cytometer of FIG. 1, according to embodiments of the present disclosure.

In some embodiments, imaging device 123 may be operably connected to a controller (not shown) having a processor and a computer-readable medium that stores instructions or operational steps. These instructions or steps, when executed by the processor, may post-process the 2-D or 3-D images produced by imaging device 123. For example, the processor may correct for measured optical aberrations from the channel 119, combine 2-D images from imaging device 123 into a 3-D image, and/or adjust the contrast, brightness, etc. of the images FIG. 3 is a schematic representation of an exemplary set of optical elements 102' for forming light sheet 106 for exemplary flow cytometer 100 of FIG. 1. As shown in FIG. 3, excitation light 301 emitted from the light source (not shown) may pass through a scanner 303, an f-theta lens 305, and a tube lens 307, which may form light sheet 309 from excitation light 301.

Figure 4:
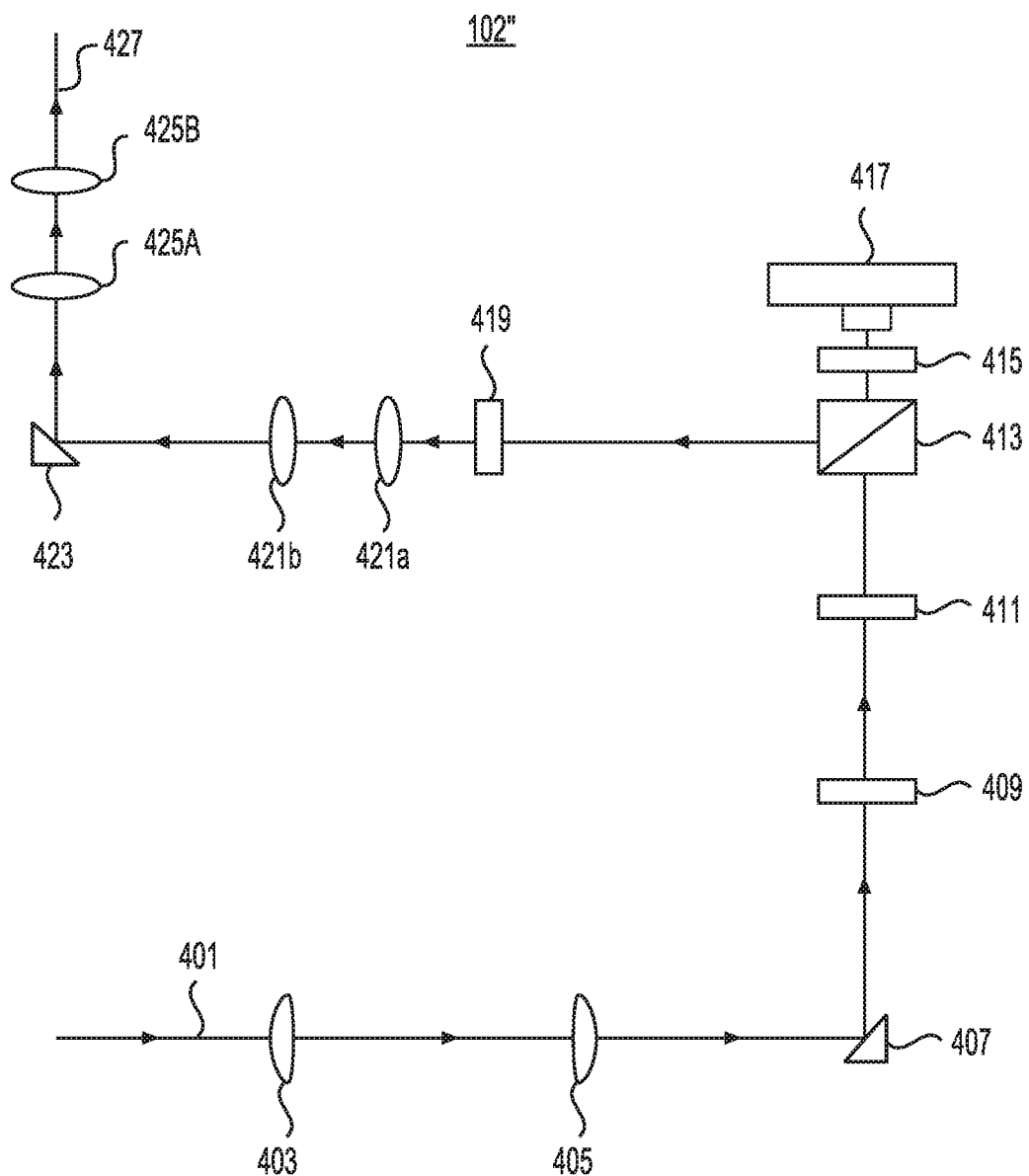
FIG. 4 is a schematic representation of another exemplary set of optical elements for forming the light sheet for the exemplary flow cytometer of FIG. 1, according to embodiments of the present disclosure.

FIG. 4 is a schematic representation of another exemplary set of optical elements 102" for forming light sheet 106 for exemplary flow cytometer 100 of FIG. 1. As shown in FIG. 4, excitation light 401 emitted from the light source (not shown) may pass through one or more x-cylindrical lenses, e.g., lenses 403 and 405, one or more z-cylindrical lenses, e.g., lenses 409 and 411, a partial beam splitter 413, a wave plate 415, a spatial light modulator 417, a mask 419, and one or more galvos, e.g., z galvo 421a and 421b, and x galvo 425a and 425b, which may form light sheet 427 from excitation light 401. In some embodiments, the excitation light may pass through one or more mirrors, e.g., mirrors 407 and 423.

Figure 5:
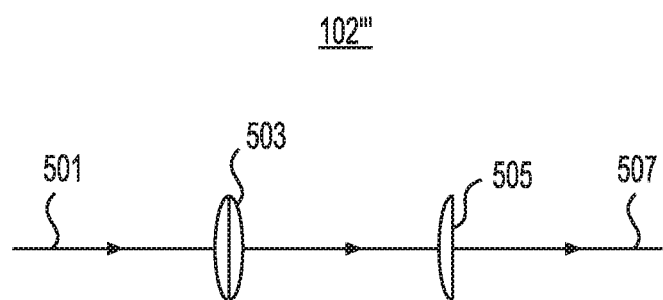
FIG. 5 is a schematic representation of yet another exemplary set of optical elements for forming the light sheet for the exemplary flow cytometer of FIG. 1, according to embodiments of the present disclosure.

FIG. 5 is a schematic representation of yet another exemplary set of optical elements 102''' for forming the light sheet for exemplary flow cytometer 100 of FIG. 1. As shown in FIG. 5, excitation light 501 emitted from the light source (not shown) may pass through a collimator 503 and a cylindrical lens 505, which may form light sheet 507 from excitation light 501.

Figure 6:
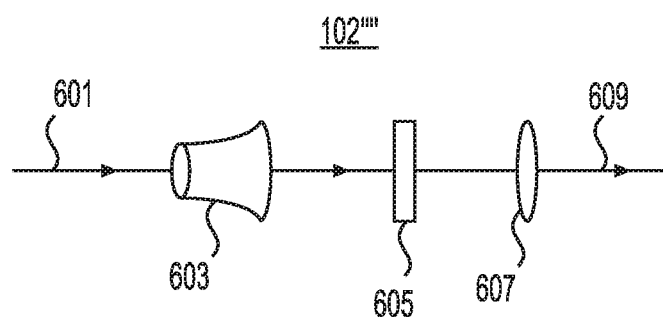
FIG. 6 is a schematic representation of yet another exemplary set of optical elements for forming the light sheet for the exemplary flow cytometer of FIG. 1, according to embodiments of the present disclosure.

FIG. 6 is a schematic representation of yet another exemplary set of optical elements 102"" for forming the light sheet for the exemplary flow cytometer of FIG. 1. As shown in FIG. 6, excitation light 601 may pass through a cylindrical beam expander 603, a rectangular slit 605, and one or more lenses, e.g., lens 607, which may form light sheet 609 from excitation light 601.

Figure 7A:
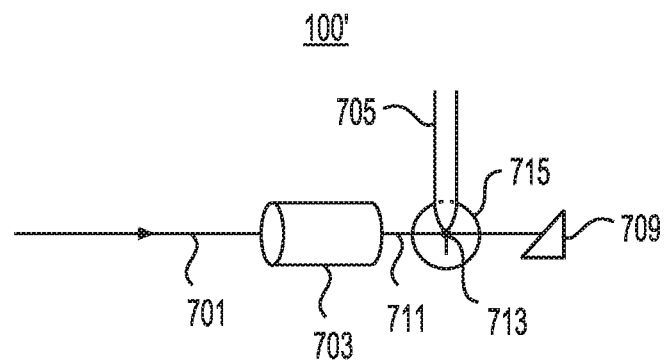
FIG. 7a is a schematic representation of a side view of an exemplary modification of the flow cytometer imaging system, according to embodiments of the present disclosure.
Figure 7B:
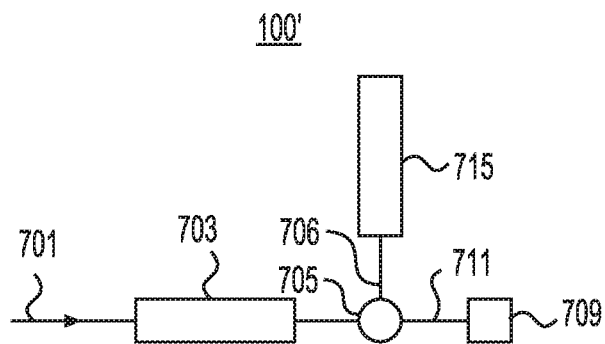
FIG. 7b is a schematic representation of a top view of the exemplary modification of the flow cytometer imaging system depicted in FIG. 7a, according to embodiments of the present disclosure.

FIG. 7a is a schematic representation of a side view of an exemplary modification of the flow cytometer imaging system 100'. As described above, illumination light sheet 114 may pass through the sample 115 of the exemplary flow cytometer 100 of FIG. 1. As shown in FIG. 7a, illumination light sheet 701 may be focused on sample 713, which may be contained in microfluidic channel 705, by objective 703. Mirror 709 may be used to form a standing wave 711, which may induce emission light (not shown) from sample 713. The emission light may be collected and/or focused by detection objective 713 before reaching the imaging device (not shown). FIG. 7b is a schematic representation of a top view of the modification 100' shown in FIG. 7a. FIG. 7b shows emission light 706, which is not show in FIG. 7a.

Figure 8:
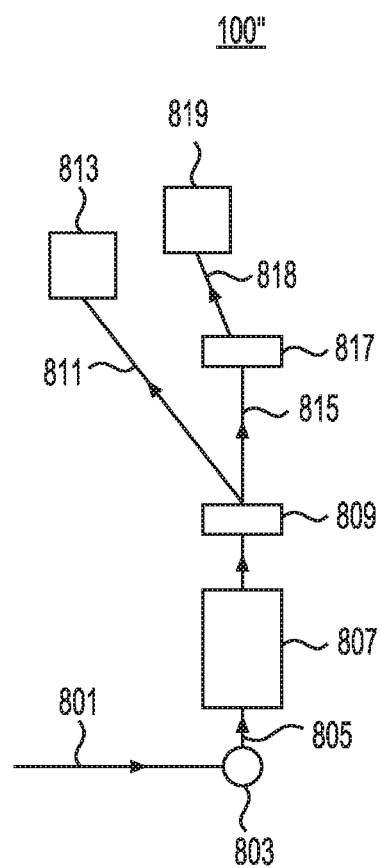
FIG. 8 is a schematic representation of an additional exemplary modification of the flow cytometer imaging system, according to embodiments of the present disclosure.

FIG. 8 is a schematic representation of a top view of an additional exemplary modification of the flow cytometer imaging system 100". As described above, illumination light sheet 114 may pass through sample 115 of the exemplary flow cytometer 100 of FIG. 1. As shown in FIG. 8, illumination light sheet 801 may be focused on sample 803, which may induce emission light 805 from sample 803. The emission light may be collected and/or focused by detection objective 807. Emission light 805 may be split by one or more dichroic filters, e.g., filters 809 and 817, and directed to one or more imaging devices, e.g., devices 813 and 819. In the example shown in FIG. 8, emission light 805 may be split by a first dichroic filter 809 such that one portion 811 of the emission light 805 is directed to a first imaging device 813 and a second portion 815 is directed to a second dichroic filter 817. The second portion 815 may be further split by the second dichroic filter 817 such that a third portion 818 of the second portion 815 may be directed to a second imaging device 819 and a fourth portion (not shown) of the second portion 815 may be directed elsewhere. Increasing the number of dichroic filters and imaging devices may allow for obtaining additional 2-D images corresponding to the one or more colors selected by the one or more dichroic filters.

Figure 9:
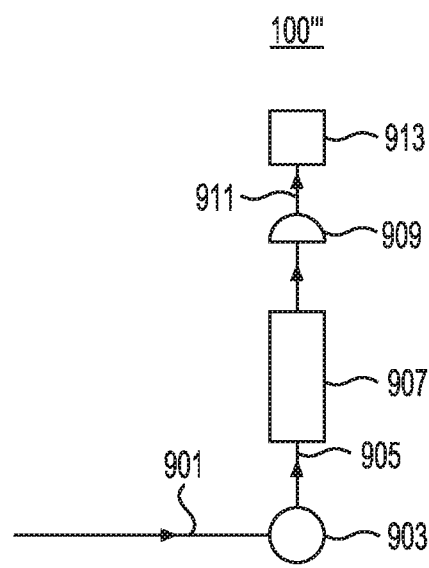
FIG. 9 is a schematic representation of an additional exemplary modification of the flow cytometer imaging system, according to embodiments of the present disclosure.

FIG. 9 is a schematic representation of a top view of an additional exemplary modification of the flow cytometer imaging system 100'''. As described above, illumination light sheet 114 may pass through the sample 115 of exemplary flow cytometer 100 of FIG. 1. As shown in FIG. 9, light sheet 901 may be focused on sample 903, which may induce emission light 905 from sample 903. Emission light 905 may be collected and/or focused by detection objective 907. Emission light 905 may pass through a filtering device 909, which may be configured to select an emission spectral band 911 to direct to imaging device 913. Filtering device 909 may include, for example, a filter wheel or a liquid crystal filter.

Figure 10:
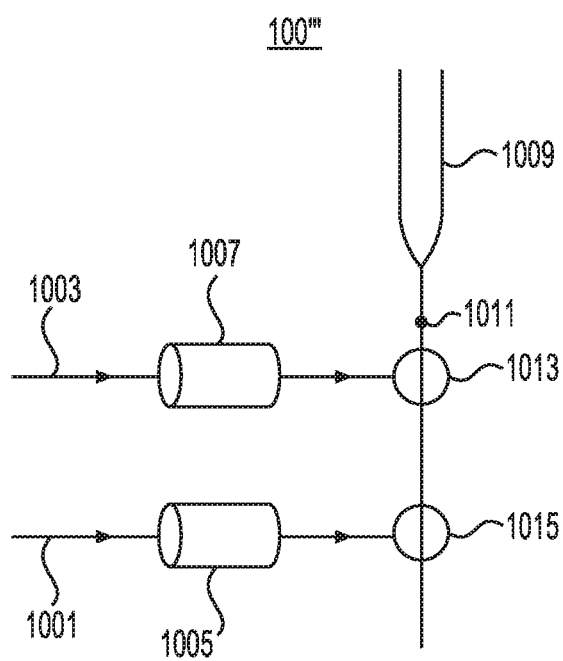
FIG. 10 is a schematic representation of an additional exemplary modification of the flow cytometer imaging system, according to embodiments of the present disclosure.

FIG. 10 is a schematic representation of a side view of an additional exemplary modification of the flow cytometer imaging system 100'''. As described above, light source 101 of exemplary flow cytometer 100 of FIG. 1 may include a plurality of light sources. In the example shown in FIG. 10, a plurality of light sources and a plurality of sets of optical elements (not shown) may form a plurality of light sheets, e.g., sheets 1001 and 1003. Light sheet 1001 may be focused on sample 1011, which may be contained in microfluidic channel 1009, by objective 1005. Similarly, light sheet 1003 may be focused on sample 1011, which may be contained in microfluidic channel 1009, by objective 1007. Light sheet 1003 may induce emission light (not shown) from sample

1011. The emission light may be collected and/or focused by detection objective 1013 before reaching a first imaging device (not shown). Similarly, light sheet 1001 may induce emission light (not shown) from sample 1011. The emission light may be collected and/or focused by detection objective 1015 before reaching a second imaging device (not shown). Increasing the number of light sheets, detection objectives, and imaging devices may allow for obtaining additional 2-D images. Advantageously, each light sheet may include a different spectrum, which may allow obtaining additional 2-D images corresponding to the different spectra of the plurality of light sheets.

Figure 11:
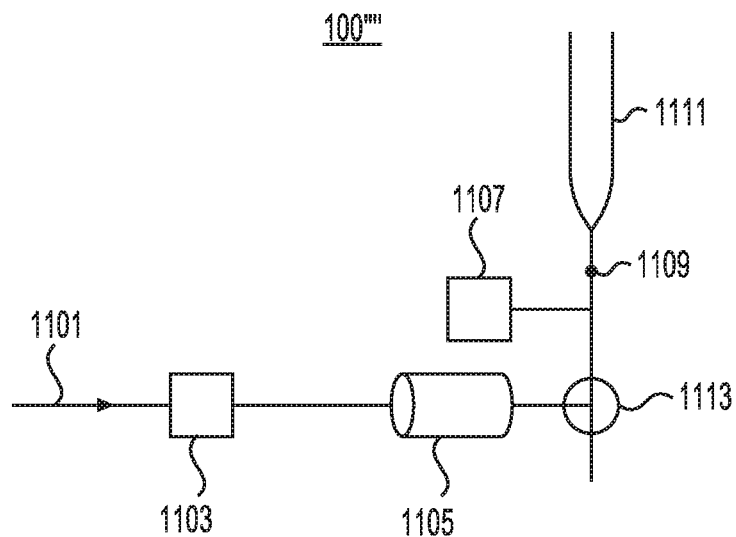
FIG. 11 is a schematic representation of an additional exemplary modification of the flow cytometer imaging system, according to embodiments of the present disclosure.

FIG. 11 is a schematic representation of a side view of an additional exemplary modification of the flow cytometer imaging system 100''''. As described above, illumination light sheet 114 may pass through sample 115 of exemplary flow cytometer 100 of FIG. 1. As shown in FIG. 11, switch 1103 may turn light sheet 1101 on and off. Switch 1103 may include, for example, an acousto-optic deflector or optical shutter. Advantageously, the switch may allow obtaining 2-D images of selected planes of sample 1109. In the example shown in FIG. 11, objective 1005 may focus the light sheet 1101 on the sample 1109, which may be contained in microfluidic channel 1111. Objective 1113 may collect and/or focus the emitted light (not shown) from sample 1109 before reaching a first imaging device (not shown).

The example shown in FIG. 11 further includes a second imaging device 1107 adapted to image the sample before it passes through the light sheet. Second imaging device 1107 may include, for example, a widefield camera. Advantageously, second imaging device 1107 may allow for effective selection of illumination planes using switch 1103. Additionally, second imaging device 1107 may allow for correction of the images from the first imaging device (not shown) caused by rotation of sample 1109 in microfluidic channel 1111.

Figure 12:
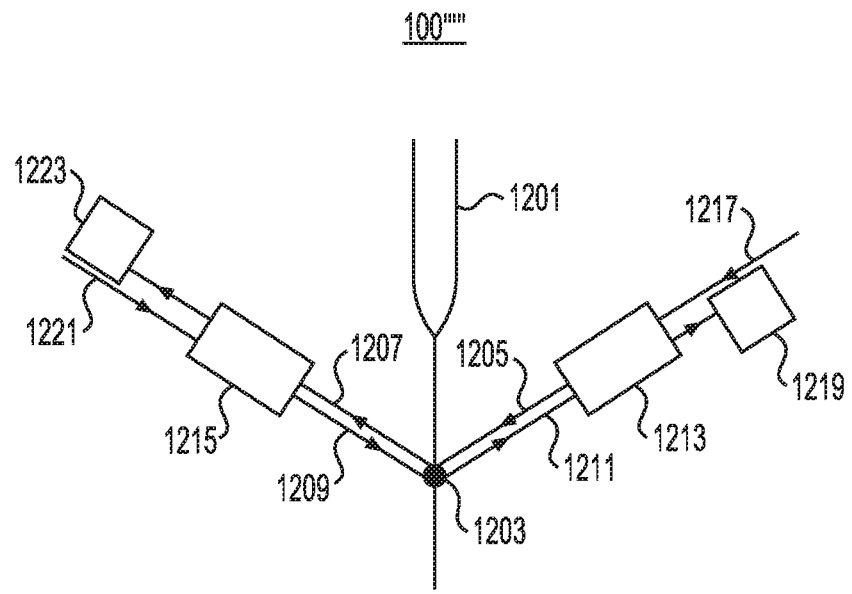
FIG. 12 is a schematic representation of an additional exemplary modification of the flow cytometer imaging system, according to embodiments of the present disclosure.

FIG. 12 is a schematic representation of a side view of an additional exemplary modification of the flow cytometer imaging system 100'''''. As described above, illumination light sheet 114 may be focused by an illumination objective 113, and emission light 116 may be focused by detection objective 117 of exemplary flow cytometer 100 of FIG. 1. As shown in FIG. 12, a plurality of light sources (not shown) may emit a plurality of excitation light beams (not shown), which may be used to form a plurality of light sheets, e.g., sheets 1217 and 1221. In the example of FIG. 12, objective 1215 may both focus light sheet 1221 into illumination light sheet 1209 and also collect and/or focus emission light 1207 toward imaging device 1223. Similarly, objective 1213 may both focus light sheet 1217 into illumination light sheet 1205 and also collect and/or focus emission light 1211 toward imaging device 1219. Illumination light sheet 1209 may induce emission light 1211 from sample 1203, which may be imaged by imaging device 1219. Similarly, illumination light sheet 1205 may induce emission light 1207 from sample 1203, which may be imaged by imaging device 1223. Sample 1203 may be contained in microfluidic channel 1201.

Figure 13:
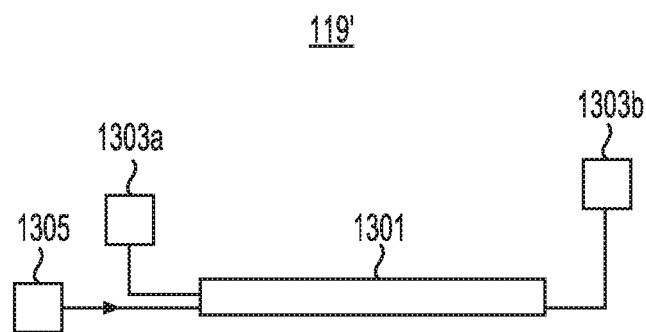
FIG. 13 is a schematic representation of an exemplary microfluidic channel for the exemplary flow cytometer of FIG. 1, according to embodiments of the present disclosure.

FIG. 13 is a schematic representation of an exemplary microfluidic channel 119' for the exemplary flow cytometers 100, 100', 100'', 100''', 100'''', and 100''''' of FIGS. 1, 7a, 7a, 8, 9, 10, 11, and 12. As shown in FIG. 13, microfluidic channel 119' may include a chamber 1301 and a pumping device, which may include a first portion 1303a and a second portion 1303b. The pumping device may include, for example, a pressure pump, a syringe pump, a peristaltic pump, an electro-osmotic pump, a pierzoelectric pump, or any other appropriate pump. The pumping device may also include a DC electric field generator. In the example shown in FIG. 13, optical tweezers 1305 may reduce rotation of the sample (not shown) as it flows through chamber 1301.

Figure 14:
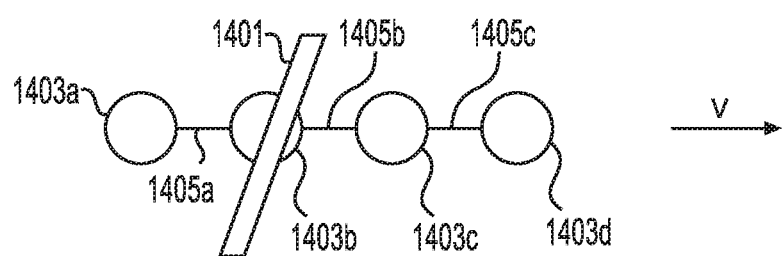
FIG. 14 is a schematic cross-sectional illustration of an example of a light sheet passing through an identification tag composed of a plurality of beads, according to embodiments of the present disclosure.

FIG. 14 is a schematic cross-sectional illustration of an example of a light sheet passing through an identification tag composed of beads included in sample 115 of exemplary flow cytometer 100. As described above, illumination light sheet 114 may pass through sample 115 of exemplary flow cytometer 100 of FIG. 1. As shown in FIG. 14, light sheet 1401 may be focused on a sample (not shown). The sample may include a sequence of a plurality of beads, e.g., beads 1403a, 1403b, 1403c, and 1403d, connected by a segmented backbone, e.g., segments 1405a, 1405b, 1405c, and 1405d. The imaging device (not shown) may generate successive 2-D images of planes of the sample (not shown), which may be post-processed to form a 3-D image of the sample which shows the sequence of a plurality of beads.

Figure 15:
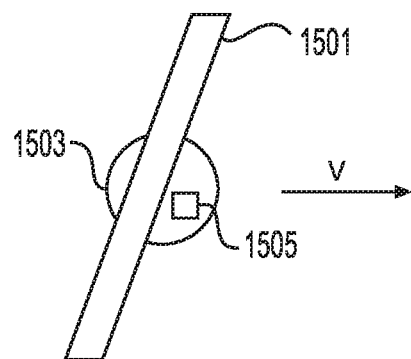
FIG. 15 is a schematic cross-sectional illustration of an example of a light sheet passing through an identification tag composed of at least one barcode, according to embodiments of the present disclosure.

FIG. 15 is a schematic cross-sectional illustration of an example of a light sheet passing through an identification tag composed of at least one barcode included in sample 115 of exemplary flow cytometer 100. As described above, illumination light sheet 114 may pass through sample 115 of exemplary flow cytometer 100 of FIG. 1. As shown in FIG. 15, light sheet 1501 may be focused on a sample (not shown). The sample may include one or more beads, e.g., bead 1503, which may contain one or more barcodes, e.g., code 1505.

Advantageously, sequencing technologies such as DropSeq 10× genomics, 454 sequencing, and other comparable technologies already use beads to collect and/or sort copied sequences from samples. In some embodiments, pre-existing technologies that use beads may be adapted to use beads including identification tags, such as a barcode, which may allow the sequences copied from a sample to be associated with 3-D images of the same sample.

The imaging device (not shown) may generate successive 2-D images of planes of the sample (not shown), which may be post-processed to form a 3-D image of the sample which shows the one or more barcodes contained on the one or more beads. Advantageously, visibility of the identification tag may allow for the association with a previous sequencing, as explained above.

Figure 16:
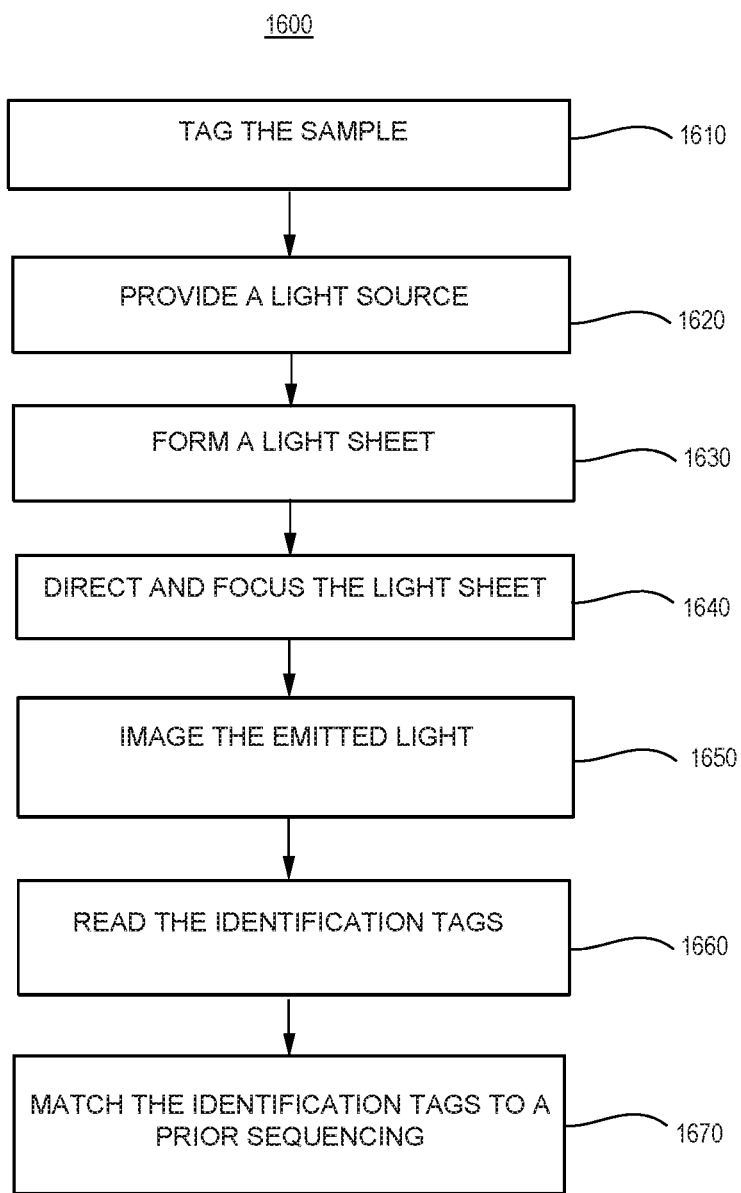
FIG. 16 is a flowchart of an exemplary method for obtaining a 3-D image showing an identification tag, according to embodiments of the present disclosure.

The flow cytometer imaging system as described herein may be utilized in a variety of methods. FIG. 16 is a flowchart of an exemplary method 1600 for imaging a sample including identification tags. Method 1600 uses the flow cytometer imaging system and of the embodiments of the system described above in reference to FIG. 1.

At step 1610, sample 115 is tagged with one or more identification tags. For example, the one or more identification tags may each include a plurality of beads that may be spatially arranged in a well-defined fashion and may be strung together by a backbone. In other instances, the one or more identification tags may each include at least one bead adapted to having a barcode printed thereon.

At step 1620, light source 101 is provided and configured to emit excitation light 104 having one or more wavelengths. For example, a plurality of lights sources may emit a plurality of excitation lights. In other instances, the plurality of excitation lights may include different spectra.

At step 1630, a set of optical elements 102 forms light sheet 106 from excitation light 104. For example, the set of optical elements 102 may dither a Gaussian beam and may include any number of laser scanners, an f-theta lens, and a tube lens. In other instances, the set of optical elements 102 may form a lattice light sheet and may include any number of cylindrical lenses, a beam splitter, a wave plate, a spatial light modulator, a mask, and any number of galvos. In other instances, the set of optical elements 102 may focus a Gaussian beam and may include a collimator and a cylindrical lens. In other instances, the set of optical elements may include a cylindrical beam expander, a rectangular slit, and any number of lenses.

At step 1640, a scanner 103, one or more mirrors, e.g., mirrors 105 and 10, and one or more lenses, e.g., lenses 107 and 111, may direct and/or focus light sheet 106 to objective 113; objective 113 may focus light sheet 106 toward sample 115; and illumination light sheet 114 may induce emission light 116 from sample 115. For example, a plurality of objectives may focus a plurality of light sheets. In some instances, the plurality of light sheets may include different spectra. In some instances, emission light 116 may be single- or multi-colored, depending on illumination light sheet 114. In some instances, a plurality of illumination light sheets may induce a plurality of emission lights. In some instances, the plurality of emission lights may include different spectra.

At step 1650, objective 117 may collect and/or focus emission light 116; one or more lenses, e.g., lens 125, and one or more mirrors, e.g., mirror 121, may direct and/or focus emission light 116 to imaging device 123; and imaging device 123 may form a 2-D image of one plane of sample 115 from emission light 116. In some instances, imaging device 123 may capture a plurality of emission lights and form a plurality of 2-D images of a plurality of planes of sample 115 from the plurality of emission lights. In some instances, imaging device 123 may use successive 2-D images to render a 3-D image of sample 115.

At step 1660, the identifications tags included in sample 115 may be read from the 3-D image. For example, the identification tags visible in the 3-D image may be read by a processor executing instructions or operational steps stored on a computer-readable medium.

At step 1670, the identification tags included in sample 115 and read from the 3-D image may be matched to previous information correlated with the identification tags. For example, the identification tags may be correlated with a previous sequencing of sample 115. In some instances, the correlation may be performed by a processor executing instructions or operational steps stored on a computer-readable medium.

Method 1600 may further include additional steps. For example, method 1600 may include sequencing sample 115 before tagging sample 115. In some instances, a sequencing assay may be used to sequence sample 115 and may be used to tag sample 115 with identification tags corresponding to different sequences. For example, the sequencing assay may be adapted for DropSeq technology, 10× genomics, 454 sequencing, or another known method using bead-bound oligonucleotides for capturing and analyzing genomic or transcriptional information (whether in a droplet or on a pico-titer plate).

Method 1600 may further include post-processing the 2-D images before rendering a 3-D image of sample 115. For example, imaging device 123 may be operably connected to a controller having a processor and a computer-readable medium that stores instructions or operational steps. These instructions or steps, when executed by the processor, may post-process the 2-D images to, for example, reduce optical aberrations; adjust brightness, contrast, etc.; or smooth textures.

Method 1600 may further include post-processing the 3-D image of sample 115. For example, imaging device 123 may be operably connected to a controller having a processor and a computer-readable medium that stores instructions or operational steps. These instructions or steps, when executed by the processor, may post-process the 3-D image to, for example, reduce optical aberrations; adjust brightness, contrast, etc.; smooth textures; or perform depth correction.

Figure 17:
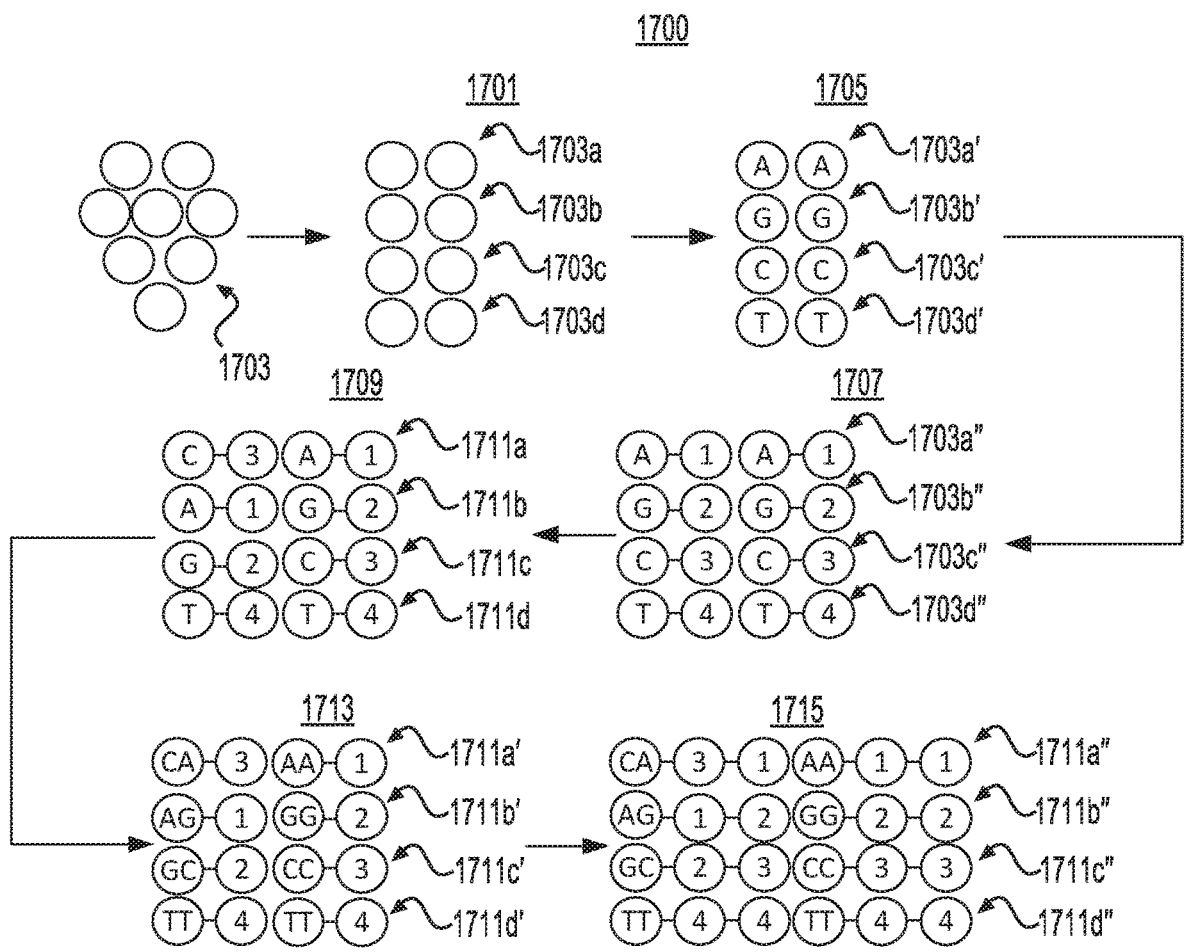
FIG. 17 is a flowchart of an exemplary method for manufacturing identification tags, according to embodiments of the present disclosure.

The identification tags as described in step 1610 of method 1600 may be manufactured in a variety of methods. FIG. 17 is a flowchart of an exemplary method 1700 for manufacturing identification tags. In the example of FIG. 17, the one or more identification tags each includes a plurality of beads. Moreover, the example of FIG. 17 may be adapted for DropSeq technology, 10x genomics, 454 sequencing, or another known method using bead-bound oligonucleotides for capturing and analyzing genomic or transcriptional information (whether in a droplet or on a pico-titer plate).

At step 1701, a plurality of beads, e.g., plurality 1703, may be divided into a first set of four groups, e.g., groups 1703*a*, 1703*b*, 1703*c*, and 1703*d*. In the example of FIG. 17, plurality 1703 includes eight beads. Preferably, the number of beads in plurality 1703 may be equal to or greater than the number of cells in the sample.

At step 1705, each of the four groups, e.g., groups 1703*a*, 1703*b*, 1703*c*, and 1703*d*, is tagged with one of adenine (A), guanine (G), cytosine (C), or thymine (T). For example, group 1703*a* may be tagged with A, becoming group 1703*a*'; group 1703*b* may be tagged with G, becoming group 1703*b*'; group 1703*c* may be tagged with C, becoming group 1703*c*'; and group 1703*d* may be tagged with T, becoming group 1703*d*'. In the example of FIG. 17, each group includes two beads. Preferably, the number of beads in each group may be approximately equal to one-fourth of the total number of beads in plurality 1703.

At step 1707, each of the four groups, e.g., groups 1703*a*', 1703*b*', 1703*c*', and 1703*d*', is tagged with an additional bead that is colored. For example, group 1703*a*' may be tagged with a bead including color 1, becoming group 1703*a*"; group 1703*b*' may be tagged with a bead including color 2, becoming group 1703*b*"; group 1703*c*' may be tagged with a bead including color 3, becoming group 1703*c*"; and group 1703*d*' may be tagged with a bead including color 4, becoming group 1703*d*". Preferably, each color may exhibit a high contrast relative to the other colors. In the example of FIG. 17, each group includes two bead chains. Preferably, the number of bead chains in each group may be approximately equal to one-fourth of the total number of beads in plurality 1703.

At step 1709, plurality 1703 is recombined and randomly separated into a second set of four groups, e.g., groups 1711*a*, 1711*b*, 1711*c*, and 1711*d*. In the example of FIG. 17, each group includes two bead chains. Preferably, the number of bead chains in each group may be approximately equal to one-fourth of the total number of beads in plurality 1703.

At step 1713, each of the four groups, e.g., groups 1711*a*, 1711*b*, 1711*c*, and 1711*d*, is tagged with one of adenine (A), guanine (G), cytosine (C), or thymine (T). For example, group 1711*a* may be tagged with A, becoming group 1711*a*'; group 1711*b* may be tagged with G, becoming group 1711*b*'; group 1711*c* may be tagged with C, becoming group 1711*c*'; and group 1711*d* may be tagged with T, becoming group 1711*d*'. In the example of FIG. 17, each group includes two bead chains. Preferably, the number of bead chains in each group may be approximately equal to one-fourth of the total number of beads in plurality 1703.

At step 1715, each of the four groups, e.g., groups 1711*a*', 1711*b*', 1711*c*', and 1711*d*', is tagged with an additional bead that is colored. For example, group 1711*a*' may be tagged with a bead including color 1, becoming group 1711*a*"; group 1711*b*' may be tagged with a bead including color 2, becoming group 1711*b*"; group 1711*c*' may be tagged with a bead including color 3, becoming group 1711*c*"; and group 1711*d*' may be tagged with a bead including color 4, becoming group 1711*d*". Preferably, each color may exhibit a high contrast relative to the other colors. In the example of FIG. 17, each group includes two bead chains. Preferably, the number of bead chains in each group may be approximately equal to one-fourth of the total number of beads in plurality 1703.

Steps 1709, 1713, and 1715 may be repeated. For example, steps 1709, 1713, and 1715 may be repeated such that each bead chain includes a nucleotide sequence of length twelve and a colored bead sequence of length twelve. Because the number of possible sequences scales with the power of four, a sequence length of twelve may allow for 16,777,216 possible permutations.

Advantageously, this method may allow for identification of the sequencing of each cell within the sample using the nucleotide sequence as a first identification tag and may allow for identification of the imaging of each cell within the sample using the bead sequence as a second identification tag.

Figure 18:
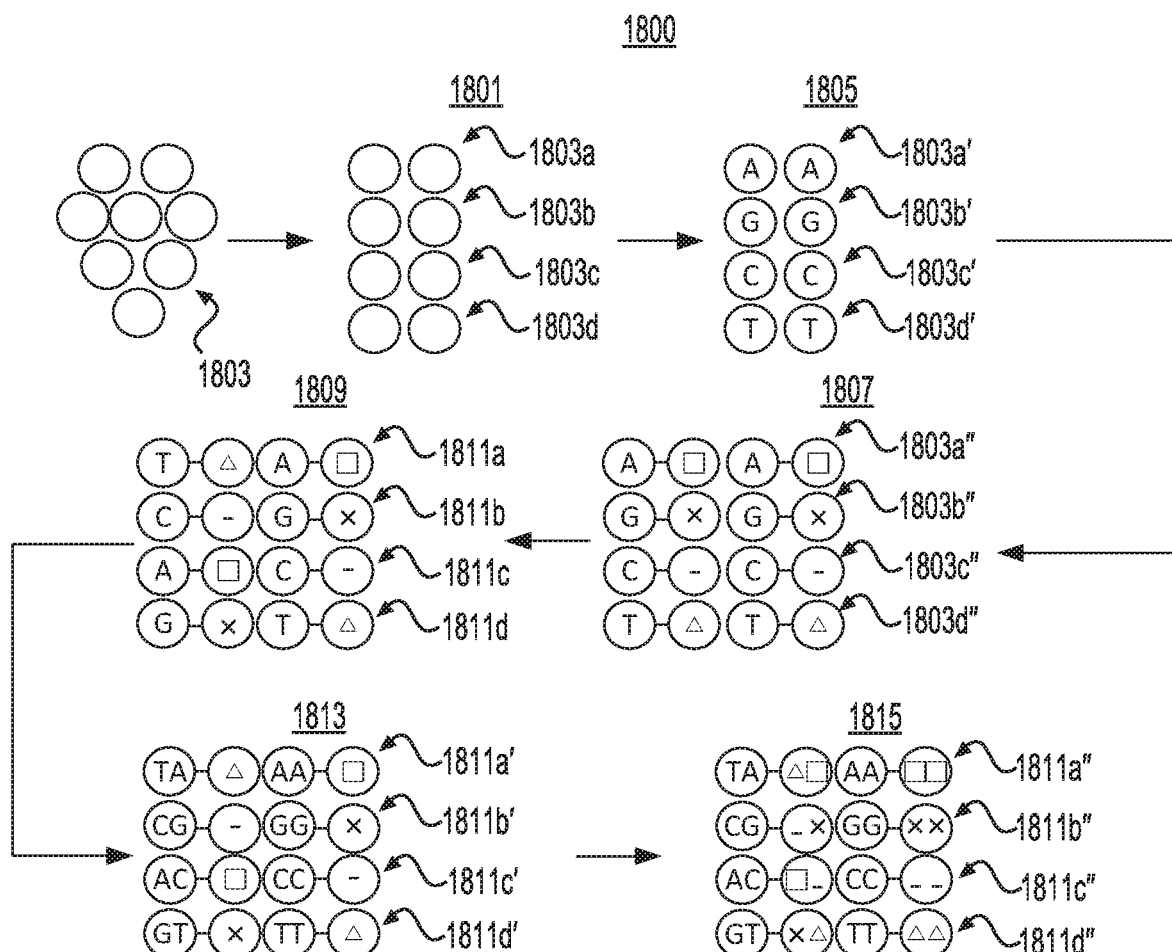
FIG. 18 is a flowchart of an additional exemplary method for manufacturing identification tags, according to embodiments of the present disclosure.

FIG. 18 is a flowchart of an additional exemplary method 1800 for manufacturing identification tags. In the example of FIG. 18, the one or more identification tags each includes at least one bead adapted to having a barcode printed thereon. Moreover, the example of FIG. 18 may be adapted for DropSeq technology, 10× genomics, 454 sequencing, or another known method using bead-bound oligonucleotides for capturing and analyzing genomic or transcriptional information (whether in a droplet or on a pico-titer plate).

At step 1801, a plurality of beads, e.g., plurality 1803, may be divided into a first set of four groups, e.g., groups 1803*a*, 1803*b*, 1803*c*, and 1803*d*. In the example of FIG. 18, plurality 1803 includes eight beads. Preferably, the number of beads in plurality 1803 may be equal to or greater than the number of cells in the sample.

At step 1805, each of the four groups, e.g., groups 1803*a*, 1803*b*, 1803*c*, and 1803*d*, is tagged with one of adenine (A), guanine (G), cytosine (C), or thymine (T). For example, group 1803*a* may be tagged with A, becoming group 1803*a*'; group 1803*b* may be tagged with G, becoming group 1803*b*'; group 1803*c* may be tagged with C, becoming group 1803*c*'; and group 1803*d* may be tagged with T, becoming group 1803*d*'. In the example of FIG. 18, each group includes two beads. Preferably, the number of beads in each group may be approximately equal to one-fourth of the total number of beads in plurality 1803.

At step 1807, each of the four groups, e.g., groups 1803*a*', 1803*b*', 1803*c*', and 1803*d*', is tagged with an additional bead containing a photobleached pattern. For example, group 1803*a*' may be tagged with a bead including a square pattern, becoming group 1803*a*"; group 1803*b*' may be tagged with a bead including an 'X' pattern, becoming group 1803*b*"; group 1803*c*' may be tagged with a bead including a line pattern, becoming group 1803*c*"; and group 1803*d*' may be tagged with a bead including a triangle pattern, becoming group 1803*d*". Preferably, each pattern may be distinct from the other patterns. In the example of FIG. 18, each group includes two bead chains. Preferably, the number of bead chains in each group may be approximately equal to one-fourth of the total number of beads in plurality 1803.

At step 1809, plurality 1803 is recombined and randomly separated into a second set of four groups, e.g., groups 1811*a*, 1811*b*, 1811*c*, and 1811*d*. In the example of FIG. 18, each group includes two bead chains. Preferably, the number of bead chains in each group may be approximately equal to one-fourth of the total number of beads in plurality 1803.

At step 1813, each of the four groups, e.g., groups 1811*a*, 1811*b*, 1811*c*, and 1811*d*, is tagged with one of adenine (A), guanine (G), cytosine (C), or thymine (T). For example, group 1811*a* may be tagged with A, becoming group 1811*a*'; group 1811*b* may be tagged with G, becoming group 1811*b*'; group 1811*c* may be tagged with C, becoming group 1811*c*'; and group 1811*d* may be tagged with T, becoming group 1811*d*'. In the example of FIG. 18, each group includes two bead chains. Preferably, the number of bead chains in each group may be approximately equal to one-fourth of the total number of beads in plurality 1803.

At step 1815, the additional bead each of the four groups, e.g., groups 1811*a*', 1811*b*', 1811*c*', and 1811*d*', is photobleached with an additional pattern. For example, the additional beads of group 1811*a*' may be bleached with a square pattern, becoming group 1811*a*"; the additional beads of group 1811*b*' may be bleached with an 'X' pattern, becoming group 1811*b*"; the additional beads of group 1811*c*' may be bleached with a line pattern, becoming group 1811*c*"; and the additional beads of group 1811*d*' may be bleached with a triangle pattern, becoming group 1811*d*". Preferably, each pattern may be distinct from the other patterns. In the example of FIG. 18, each group includes two bead chains. Preferably, the number of bead chains in each group may be approximately equal to one-fourth of the total number of beads in plurality 1803.

Steps 1809, 1813, and 1815 may be repeated. For example, steps 1809, 1813, and 1815 may be repeated such that each bead chain includes a nucleotide sequence of length twelve and an additional bead with a pattern of length twelve. Because the number of possible sequences scales with the power of four, a sequence length of twelve may allow for 16,777,216 possible permutations.

Advantageously, this method may allow for identification of the sequencing of each cell within the sample using the nucleotide sequence as a first identification tag and may allow for identification of the imaging of each cell within the sample using the photobleached pattern on the additional bead as a second identification tag.

Method 1800 may further include additional steps. For example, method 1800 may include tagging each group with two or more additional beads, each containing a photobleached pattern. Advantageously, the redundancy of the additional beads may allow for easier identification of the imaging of each cell within the sample. For example, if one of the additional beads is somehow obstructed in the imaging of the cells, the other of the additional beads may still be visible, allowing identification.

Advantageously, methods 1600, 1700, 1800, or any combination thereof, may allow significant breakthroughs in at least the fields of microbiology and genetics. For example, association of 3-D images of a sample with the sequencing of that sample may permit direct observation of how various gene sequences result in varying intracellular structures and interactions. Such direct observation may result in, for example, more sophisticated understandings of drug uptake in microorganisms, which may result in more sophisticated understandings of how microorganisms develop immunity to and otherwise interact with pharmaceuticals and other drugs.

Association of 3-D images of a sample with the sequencing of that sample may also permit, for example, observation and study of how various gene sequences affect cell phagocytosis. Such observation and study may result in, for example, more sophisticated understandings of the interaction between immune systems and pathogens.

Association of 3-D images of a sample with the sequencing of that sample may also permit, for example, observation and study of how various gene sequences affect cell signaling. Such observation and study may result in, for example, more sophisticated understandings of how and why cell signaling may break down, which may result in more sophisticated understandings of the causes of cancer, autoimmunity, diabetes, dementia, and other diseases caused by errors in cell signaling.

Association of 3-D images of a sample with the sequencing of that sample may also permit, for example, observation and study of how various gene sequences affect cell autophagy. Such observation and study may result in, for example, more sophisticated understandings of how and why cell degradation may break down, which may result in more sophisticated understandings of the causes of Parkinson disorder and other diseases caused by errors in cell autophagy.

Association of 3-D images of a sample with the sequencing of that sample may also permit, for example, direct observation of cellular phenotypic manifestations of genotypic differences. Such observation and study may result in, for example, more sophisticated understandings of how genetic mutations resulted in the phenotypic changes observed in the evolutionary record.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented with hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for an imaging flow cytometer, comprising:
   a light source configured to emit light having one or more wavelengths;
   at least one optical element adapted to form a light sheet from the emitted light;
   an illumination objective;
   a microfluidic channel within a focus of the light sheet and configured to hold a sample;
   a mirror adapted to reflect the light sheet focused on the sample and form a standing wave;
   a detection objective; and
   an imaging device, wherein
      the imaging device is adapted to capture light from the sample to image a two-dimensional plane of the sample while the sample is illuminated with the light sheet,
      the imaging device is adapted to form a three-dimensional image of the sample from successive two-dimensional images,
      and the imaging device is adapted to image identification tags contained within the sample.

2. The system of claim 1, further comprising:
   a plurality of dichroic filters, wherein
      the light sheet is a multi-color light sheet formed, at least in part, by the at least one optical element,
      the imaging device includes a plurality of cameras, and
      each of the plurality of dichroic filters is adapted to direct one of a plurality of spectra in the light from the sample toward a corresponding one of the plurality of cameras.

3. The system of claim 1, further comprising:
   a filtering device, wherein
      the light sheet is a multi-color light sheet formed, at least in part, by the at least one optical element, and
      the filtering device is adapted to select at least one of a plurality of emission spectral bands emitted from the sample while the sample is illuminated with the light sheet.

4. The system of claim 1, further comprising:
   a plurality of illumination objectives configured to focus respective light sheets, including the light sheet, with different illumination spectrums; and
   a plurality of detection objectives, each corresponding to a given one of the plurality of illumination objectives, wherein the imaging device includes a plurality of cameras, each corresponding to a given one of the plurality of detection objectives.

5. The system of claim 1, further comprising:
a second imaging device adapted to image the sample before the sample is imaged by the first imaging device, wherein the imaging device is the first imaging device.

6. The system of claim 1, wherein the detection objective is also adapted to function as a second illumination objective for a second light sheet, and the illumination objective is also adapted to function as a second detection objective for the second light sheet.

7. The system of claim 1, wherein the at least one optical element is adapted to form a plurality light sheets, including the light sheet, from excitation light, and the imaging device is adapted to simultaneously capture the emitted light from each of the plurality of light sheets to form the three-dimensional image.

8. The system of claim 1, further comprising:
a translation stage affixed to the detection objective, wherein
the at least one optical element is adapted to form a plurality of light sheets from the emitted light, and
the translation stage is adapted to move the detection objective to focus successive emissions from the light source for each of the plurality of light sheets.

9. The system of claim 1, further comprising:
a pump, adapted to control a flow rate in the microfluidic channel.

10. The system of claim 1, further comprising:
a DC electric field generator, adapted to pull the sample through the microfluidic chamber.

11. The system of claim 1, wherein the identification tags include a plurality of beads that are spatially arranged in a well-defined fashion.

12. The system of claim 1, wherein the identification tags include one or more beads coated with one or more photo-bleachable dyes.

13. The system of claim 1, further comprising:
a sequencing assay, wherein
the identification tags are attached to the sample during sequencing.

14. A method of imaging a sample, comprising:
attaching identification tags to a sample;
providing a light source that emits light having one or more wavelengths;
forming a light sheet from the emitted light;
directing the light sheet toward a microfluidic channel within a focus of the light sheet and configured to hold the sample containing identification tags;
forming a standing wave with the light sheet focused on the sample to induce emission light from the sample;
imaging the emission light collected from the sample, wherein each image from the imaging portrays a two-dimensional plane of the sample; and
rendering a three-dimensional image of the sample from successive two-dimensional images from the imaging, wherein the identification tags are visible in the three-dimensional image.

15. The method of claim 14, further comprising:
sequencing the sample; and
associating the sequence of the sample with the identification tags of the sample.

16. The method of claim 14, further comprising:
post-processing the successive two-dimensional images.

17. The method of claim 14, further comprising:
post-processing the rendered three-dimensional image.

18. The method of claim 14, wherein a plurality of light sources emit a plurality of lights, each having one or more wavelengths.

19. The method of claim 18, wherein a plurality of light sheets are formed from the plurality of emitted lights.

* * * * *